US009745575B2

(12) United States Patent
Patzel

(10) Patent No.: US 9,745,575 B2
(45) Date of Patent: Aug. 29, 2017

(54) ANTAGONISTS OF BACTERIAL SEQUENCES

(75) Inventor: Volker Patzel, Hanau (DE)

(73) Assignee: National University of Singapore, Singapore (SG)

( * ) Notice: Subject to any disclaimer, the term of this patent is extended or adjusted under 35 U.S.C. 154(b) by 1677 days.

(21) Appl. No.: 12/486,208

(22) Filed: Jun. 17, 2009

(65) Prior Publication Data

US 2010/0166770 A1   Jul. 1, 2010

Related U.S. Application Data

(60) Provisional application No. 61/073,860, filed on Jun. 19, 2008.

(30) Foreign Application Priority Data

Jun. 17, 2008   (EP) .................................... 08010979

(51) Int. Cl.
  *C07K 9/00*   (2006.01)
  *C07K 16/12*  (2006.01)
  *C12N 15/113* (2010.01)

(52) U.S. Cl.
  CPC ........ *C12N 15/113* (2013.01); *C12N 2310/11* (2013.01)

(58) Field of Classification Search
  None
  See application file for complete search history.

(56) References Cited

U.S. PATENT DOCUMENTS

| 7,772,386 | B1 * | 8/2010 | Jungblut et al. ............. 536/23.7 |
| 2005/0064470 | A1 | 3/2005 | Rana |
| 2008/0280848 | A1 * | 11/2008 | Patzel et al. .................... 514/44 |
| 2010/0166770 | A1 * | 7/2010 | Patzel ........................ 424/164.1 |

OTHER PUBLICATIONS

Baumann et al, Current Opinion in Immunology, 2006, 18:438-448.*
Kaufmann, Trends in Immunology, Dec. 2005, 26/12:660-667.*
Mattes et al, Am J Respir Cell Mol Biol vol. 36. pp. 8-12, 2007.*
Yang et al, Pharmacology and Therapeutics, 2008, 117:94-104.*
Zhang et al Cell Cycle 8:17, 2756-2768; Sep. 1, 2009.*
Guo et al, Advanced Drug Delivery Reviews, Apr. 30, 2010, 62/6:650-666.*
Burnett et al, Chemistry and Biology (Review), Jan. 27, 2012, pp. 60-71.*
Willkomm et al., "Evaluation of Bacterial RNase P RNA as a Drug Target", Chembiochem, 2003, 4, pp. 1041-1048.
Engdahl et al., "Introduction of an RNA Stability Element at the 5'-End of an Antisense RNA Cassette Increases the Inhibition of Target RNA Translation", Antisense & Nucleic Acid Drug Development, 11: pp. 29-40 (2001).
Lochmann et al., "Albumin-protamin-oligonucleotide nanoparticles as a new antisense delivery system. Part 1: Physiochchemical characterization", European Journal of Pharmaceutics and Biopharmaccutics, 59 (2005) pp. 419-429.
Wang et al., "An intracellular delivery method for siRNA by an arginine-rich peptide", J. Biochem. Biophys. Methods, 70 (2007) pp. 579-586.
Patzel et al., "RNA Silencing in the Struggle against Disease", Annals New York Academy of Sciences, 1082: pp. 44-46 (2006).
Carlin et al., "Monoclonal Antibodies Specific for Elongation Factor TU and Complete Nucleotide Squence of the TUF Gene in Mycobacterium Tuberculosis", Infection and Immunity, Aug. 1992, vol. 60, No. 8, pp. 3136-3142.

* cited by examiner

*Primary Examiner* — Nita M Minnifield
(74) *Attorney, Agent, or Firm* — Rothwell, Figg, Ernst & Manbeck, P.C.

(57) ABSTRACT

The present invention refers to antagonist molecules, particularly nucleic acid effector molecules directed against a bacterial RNA.

38 Claims, 16 Drawing Sheets

Fig. 6a

Figure 1:
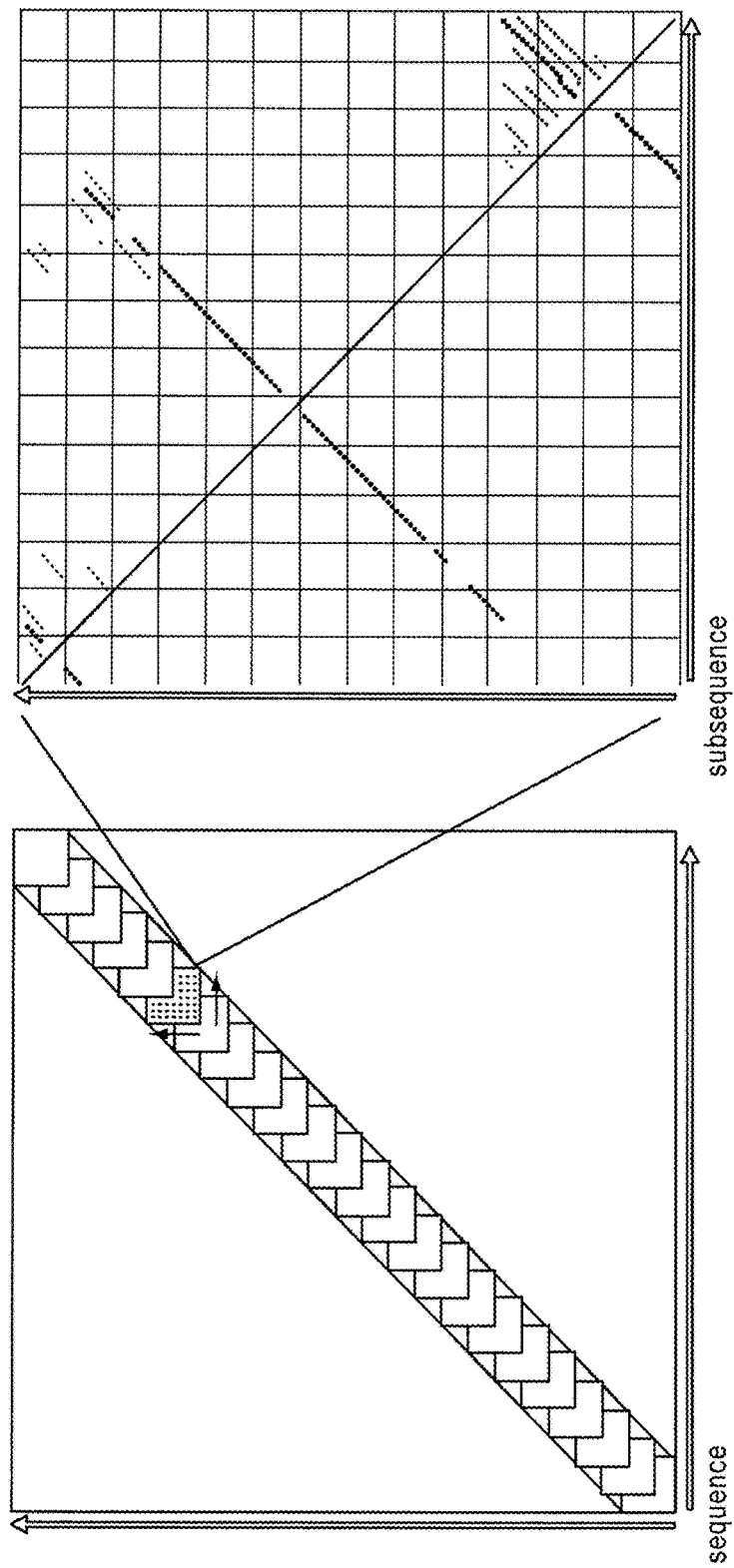

```
23mere
CAGACGCAAAAGAACAUGAUGGG 1,3
....((((.........))·))..
 AGACGCAAAAGAACAUGAUGGGC 1,3
 ...((((.........))·)))...
  GACGCAAAAGAACAUGAUGGGCG -0,8
  ..(((...............)))
   ACGCAAAAGAACAUGAUGGGCGC -1,2
   .(((...............))).

22mere
CAGACGCAAAAGAACAUGAUGG 1,3
....((((.........))·)).
 AGACGCAAAAGAACAUGAUGGC 1,3
 ...((((.........))·))..
  GACGCAAAAGAACAUGAUGGGC 1,3
  ..((((.........))·))...
   ACGCAAAAGAACAUGAUGGGCG -0,8
   .(((...............)))
    CGCAAAAGAACAUGAUGGGCGC -0,7
    (((...............))).

21mere
CAGACGCAAAAGAACAUGAUG 1,9
......((.........))...
 AGACGCAAAAGAACAUGAUGG 1,3
 ...((((.........))·)).
  GACGCAAAAGAACAUGAUGGG 1,3
  ..((((.........))·))..
   ACGCAAAAGAACAUGAUGGGC 1,3
   .((((.........))·))...
    CGCAAAAGAACAUGAUGGGCG -0,3
    (((...............)))
     GCAAAAGAACAUGAUGGGCGC 0,4
     ((...............))..

20mere
CAGACGCAAAAGAACAUGAU 1,9
......((.........))..
 AGACGCAAAAGAACAUGAUG 1,9
 .....((.........))...
  GACGCAAAAGAACAUGAUGG 1,3
  ..((((.........))·)).
   ACGCAAAAGAACAUGAUGGG 1,3
   .((((.........))·))..
    CGCAAAAGAACAUGAUGGGC 1,8
    ((((.........))·))...
     GCAAAAGAACAUGAUGGGCG 0,4
     ((...............)).
      CAAAAGAACAUGAUGGGCGC 2,0
      ........(.....).....

19mere
CAGACGCAAAAGAACAUGA 1,9
.......((.......)).
 AGACGCAAAAGAACAUGAU 2,1
 .....((.........))..
  GACGCAAAAGAACAUGAUG 1,9
  .....((.........))...
   ACGCAAAAGAACAUGAUGG 1,3
   .((((.........))·)).
    CGCAAAAGAACAUGAUGGG 1,8
    ((((.........))·))..
     GCAAAAGAACAUGAUGGGC 1,9
     .((.........))......
      CAAAAGAACAUGAUGGGCG 2,0
      ........(.....)....
       AAAAGAACAUGAUGGGCGC 2,0
       ........(.....).....
```

Fig. 6a (continued)

```
18mere
CAGACGCAAAAGAACAUG 2,3
......((.........))
 AGACGCAAAAGAACAUGA 1,2
 .....((.........)).
  GACGCAAAAGAACAUGAU 1,2
  ....((.........))..
   ACGCAAAAGAACAUGAUG 1,2
   ...((.........))...
    CGCAAAAGAACAUGAUGG 0,5
    ..........(((...)).
     GCAAAAGAACAUGAUGGG 0,5
     .........(((...))..
      CAAAAGAACAUGAUGGGC 0,5
      ........(((...))...
       AAAAGAACAUGAUGGGCG 0,5
       .......(((...))....
        AAAGAACAUGAUGGGCGC 0,5
        ........((......)).

17mere
CAGACGCAAAAGAACAU no structure
.................
 AGACGCAAAAGAACAUG 2,3
 .....((.........))
  GACGCAAAAGAACAUGA 1,2
  ....((.........)).
   ACGCAAAAGAACAUGAU 1,2
   ...((.........))..
    CGCAAAAGAACAUGAUG 1,2
    ..((.........))...
     GCAAAAGAACAUGAUGG 0,5
     .........(((...)).
      CAAAAGAACAUGAUGGG 0,5
      ........(((...))..
       AAAAGAACAUGAUGGGC 0,5
       .......(((...))...
        AAAGAACAUGAUGGGCG 0,5
        ......(((...))....
         AAGAACAUGAUGGGCGC 0,5
         .......((......)).

16mere
CAGACGCAAAAGAACA no structure
................
 AGACGCAAAAGAACAU no structure
 ................
  GACGCAAAAGAACAUG 2,3
  ....((........))
   ACGCAAAAGAACAUGA 2,3
   ...((........)).
    CGCAAAAGAACAUGAU 2,3
    ..((........))..
     GCAAAAGAACAUGAUG 2,3
     .((........))...
      CAAAAGAACAUGAUGG 0,5
      ........(((...)).
       AAAAGAACAUGAUGGG 0,5
       .......(((...))..
        AAAGAACAUGAUGGGC 0,5
        ......(((...))...
         AAGAACAUGAUGGGCG 0,5
         .....(((...))....
          AGAACAUGAUGGGCGC 0,5
          ......((......)).
```

Fig. 6b

```
23mere
GCGCCCAUCAUGUUCUUUUGCGU  -2,5
.(((................))).
 CGCCCAUCAUGUUCUUUUGCGUC  -1,0
 (((................)))..
  GCCCAUCAUGUUCUUUUGCGUCU  -0,9
  .......(((......))))..
   CCCAUCAUGUUCUUUUGCGUCUG  -0,9
   ......(((......))))...

22mere
GCGCCCAUCAUGUUCUUUUGCG  -1,2
(((................))).
 CGCCCAUCAUGUUCUUUUGCGU  -1,0
 (((................))).
  GCCCAUCAUGUUCUUUUGCGUC  -0,9
  .......(((......)))).
   CCCAUCAUGUUCUUUUGCGUCU  -0,9
   ......(((......))))..
    CCAUCAUGUUCUUUUGCGUCUG  -0,9
    .....(((......))))...

21mere
GCGCCCAUCAUGUUCUUUUGC  0,3
(((.......)))........
 CGCCCAUCAUGUUCUUUUGCG  -0,4
 .((................)).
  GCCCAUCAUGUUCUUUUGCGU  -0,8
  .......(((......))))
   CCCAUCAUGUUCUUUUGCGUC  -0,9
   ......(((......)))).
    CCAUCAUGUUCUUUUGCGUCU  -0,9
    .....(((......))))..
     CAUCAUGUUCUUUUGCGUCUG  -0,9
     ....(((......))))...

20mere
GCGCCCAUCAUGUUCUUUUG  0,3
(((.......)))........
 CGCCCAUCAUGUUCUUUUGC  1,2
 .((.......)).........
  GCCCAUCAUGUUCUUUUGCG  -0,1
  ((................)).
   CCCAUCAUGUUCUUUUGCGU  -0,8
   ......(((......))))
    CCAUCAUGUUCUUUUGCGUC  -0,9
    .....(((......)))).
     CAUCAUGUUCUUUUGCGUCU  -0,9
     ....(((......))))..
      AUCAUGUUCUUUUGCGUCUG  -0,9
      ...(((......))))...

19mere
GCGCCCAUCAUGUUCUUUU  0,3
(((.......)))......
 CGCCCAUCAUGUUCUUUUG  1,2
 .((.......)).......
  GCCCAUCAUGUUCUUUUGC  1,4
  ...((...))........
   CCCAUCAUGUUCUUUUGCG  0,0
   ........((.......)).
    CCAUCAUGUUCUUUUGCGU  -0,8
    .....(((......))))
     CAUCAUGUUCUUUUGCGUC  -0,9
     ....(((......)))).
      AUCAUGUUCUUUUGCGUCU  -0,9
      ...(((......))))..
       UCAUGUUCUUUUGCGUCUG  -0,9
       ..(((......))))...
```

Fig. 6b (continued)

```
18mere
GCGCCCAUCAUGUUCUUU  0,3
(((.......)))......
 CGCCCAUCAUGUUCUUUU  1,2
 .((........))......
  GCCCAUCAUGUUCUUUUG  1,4
  ...((...))........
   CCCAUCAUGUUCUUUUGC  1,4
   ..((...))..........
    CCAUCAUGUUCUUUUGCG  0,0
    .......((......)).
     CAUCAUGUUCUUUUGCGU  -0,8
     ....((((......))))
      AUCAUGUUCUUUUGCGUC  -0,9
      ...((((......)))).
       UCAUGUUCUUUUGCGUCU  -0,9
       ..((((......))))..
        CAUGUUCUUUUGCGUCUG  -0,9
        .((((......))))...

17mere
GCGCCCAUCAUGUUCUU  0,3
(((.......))))....
 CGCCCAUCAUGUUCUUU  1,2
 .((........)).....
  GCCCAUCAUGUUCUUUU  1,4
  ...((...))........
   CCCAUCAUGUUCUUUUG  1,4
   ..((...)).........
    CCAUCAUGUUCUUUUGC  1,4
    .((...))..........
     CAUCAUGUUCUUUUGCG  0,0
     ......((......)).
      AUCAUGUUCUUUUGCGU  -0,8
      ...((((......))))
       UCAUGUUCUUUUGCGUC  -0,9
       ..((((......)))).
        CAUGUUCUUUUGCGUCU  -0,9
        .((((......))))..
         AUGUUCUUUUGCGUCUG  -0,6
         ((((......))))...

16mere
GCGCCCAUCAUGUUCU  0,3
(((.......))) ...
 CGCCCAUCAUGUUCUU  1,2
 .((.......)) ....
  GCCCAUCAUGUUCUUU  1,4
  ...((...))......
   CCCAUCAUGUUCUUUU  1,4
   ..((...)).......
    CCAUCAUGUUCUUUUG  1,4
    .((...)).......
     CAUCAUGUUCUUUUGC  1,7
     ......((......))
      AUCAUGUUCUUUUGCG  0,0
      .....((......)).
       UCAUGUUCUUUUGCGU  -0,8
       ..((((......))))
        CAUGUUCUUUUGCGUC  -0,9
        .((((......)))).
         AUGUUCUUUUGCGUCU  -0,6
         ((((......))))..
          UGUUCUUUUGCGUCUG  -0,1
          (((......)))....
```

ANTAGONISTS OF BACTERIAL SEQUENCES

The present invention refers to antagonist molecules, particularly nucleic acid effector molecules directed against a bacterial RNA.

Until now, the presence of bacterial non-coding micro RNA molecules capable of modulating host gene expression is unknown.

By means of computational RNA secondary structure analyses we identified candidates of microRNA-like molecules originating from different mycobacteria, e.g. from *Mycobacterium tuberculosis*. Some of these bacterial RNA sequences exhibit a high degree of homology with RNA and DNA sequences of host organisms, i.e. humans, as well as with innate bacterial sequences. By reason of coincidence of sequence complementarity and miRNA-like structure we strongly assume that these sequences can successfully interfere with the hosts' or with bacterial gene expression to the advantage of the bacterial pathogen, thus, representing novel drug targets. Further, it was found that miRNA molecules derived from these bacterial sequences are capable of modulating mammalian gene expression.

Based on these findings, the present invention refers to antagonists, e.g. to nucleic acid- and nucleic acid analog-based antagonists of these novel targets and their precursors, which rely on established technologies including antisense, RNA interference, ribozyme, aptamer or antibody technologies. These antagonists are novel drug candidates with bactericidal or antibiotic activity.

In a first aspect, the present invention refers to an antagonist directed against a bacterial RNA or a precursor thereof, wherein the bacterial RNA has a stem-loop secondary structure, which resembles a micro-RNA (miRNA) structure.

In a further aspect, the present invention refers to a method for the prevention and/or treatment of a disorder caused by or associated with a bacterial pathogen, comprising administering a subject in need thereof a therapeutically effective amount of an antagonist directed against an RNA from said bacterial pathogen or against a precursor of said RNA, wherein said RNA has a stem-loop secondary structure.

A still further aspect of the present invention refers to the use of a bacterial RNA having a stem-loop secondary structure, which resembles a miRNA structure or a miRNA molecule derived from such a structure as a therapeutic or diagnostic agent.

A still further aspect of the present invention is a screening method for identifying and/or characterizing compounds which act as antagonists against a bacterial RNA or a precursor thereof, wherein the bacterial RNA has a stem-loop secondary structure, which resembles a micro-RNA (miRNA) structure.

Preferably, the stem-loop secondary structure of the bacterial target RNA is homologous to RNA or DNA host sequences and/or innate bacterial sequences. The bacterial RNA may be from mycobacteria, particularly from *M. tuberculosis*. It should be noted, however, that the RNA sequence may also be derived from other bacteria, particularly from bacteria which are capable of intracellularly infecting host cells such as *Chlamydia* spp, *Rickettsia* spp, *Salmonella* spp, *Shigella* spp, *Yersinia* spp, *E. coli*, *Mycobacterium tuberculosis*, *Listeria moncytogenes*, and *Legionella pneumophila*.

The antagonist is directed against a bacterial target RNA having a stem-loop secondary structure. The stem, i.e. a double-stranded self-complementary structure, preferably has a length of at least 10, more preferably of at least 15, and even more preferably of at least 20 base pairs. The degree of self-complementarity within the stem, i.e. the ratio of self-complementary base pairs to the whole stem length (including interruptions) is preferably at least 70%, more preferably at least 80%, and even more preferably at least 90% and up to 100% in order to obtain cleavage-competent Argonaute-2 containing RNA induced silencing complexes (RISC). The loop, i.e. the sequence connecting the two strands of the stem, preferably has a length of 3 to 20 nucleotides, more preferably from 4 to 10 nucleotides. The secondary structure of RNA molecules may be determined by suitable computer algorithms, such as mfold (by M. Zuker; all versions) and RNAfold (as part of the Vienna RNA package) including its partition function approach.

In a preferred embodiment, the stem-loop secondary structure of the bacterial target RNA is homologous to RNA or DNA host sequences, e.g. RNA or DNA from mammalian, particularly human hosts capable of being infected by the target bacterium, and/or to innate bacterial sequences. The homology of the stem-loop secondary structure to host and/or innate bacterial sequences preferably is located at least partially within the sequence portions forming the stem of the stem-loop structure. Thus, a first strand of the stem structure is homologous to a first strand of a double-stranded DNA molecule, and the sequence of the second (complementary) strand of the stem structure is homologous to the second strand (complementary to the first strand) of the DNA molecule. Correspondingly, a first strand of the stem may be homologous to an mRNA molecule, e.g. a host mRNA molecule, and a second strand of the stem is homologous to the complement of the mRNA, e.g. the host mRNA.

The length of the homology between stem sequences and host or innate bacterial sequences is preferably at least 15 bases, more preferably at least 20 bases, and even more preferably at least 25 bases for at least one strand of the stem. The degree of identity within the homologous regions is preferably at least 70%, more preferably at least 75%, even more preferably at least 80%, even more preferably, at least 85% for the strand with the highest homology. Each of the strands preferably has a degree of identity of at least 70%, and more preferably of at least 75% over a length of at least 20 bases. The identity of a bacterial target RNA to a host and/or innate bacterial sequence is calculated as follows:

$$I = n/L \times 100,$$

wherein I is the identity degree in percent, n is the number of identical nucleotides in the homologous portion of the target RNA and the host/innate bacterial sequence, and L is the total length of the homologous portion.

Figure 5:
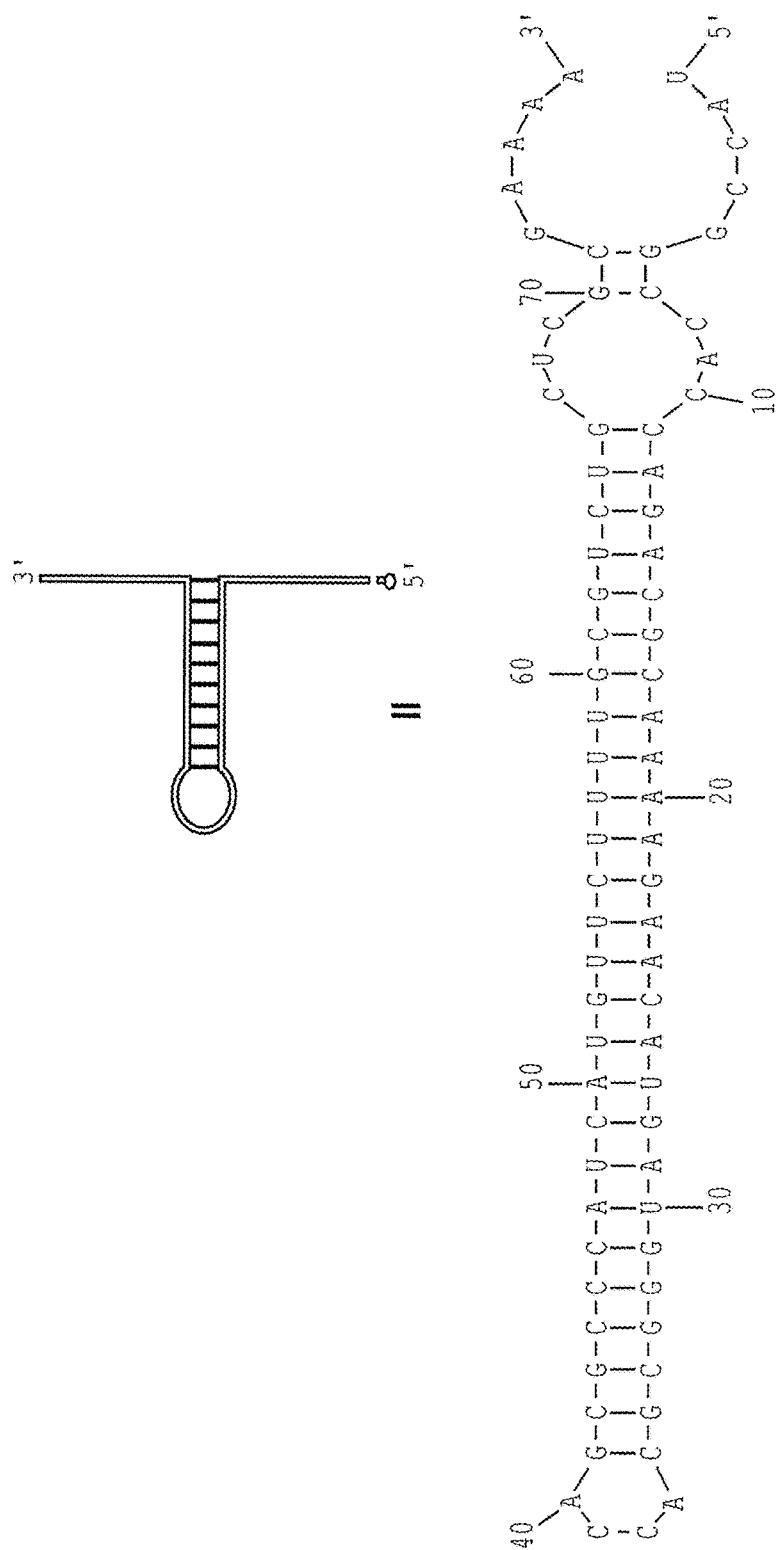

In a preferred embodiment, the antagonist of the invention is directed against an mRNA from a mycobacterial tuf gene, e.g. the tuf gene of *M. tuberculosis* (Acc. No. Rv 0685; CDC 1551 MT0713) and *M. bovis* (Acc. No. Mbovis 0704) or sequence variants thereof. Particularly, the antagonist is directed against a portion of the tuf mRNA comprising the sequence as shown in FIG. 5 (SEQ ID NO: 3).

The antagonist of the invention is particularly useful for the prevention and/or treatment of bacterial infections, particularly bacterial infections caused by or associated with intracellular bacteria, such as mycobacteria, and in particular with *M. tuberculosis*. Thus, in the preferred embodiment the antagonist is used for the prevention and/or treatment of mycobacterial infections, particularly bacterial infections caused by and/or associated with *M. tuberculosis*.

The antagonist is preferably a molecule which specifically interacts with the bacterial target RNA by inhibiting its activity to modulate gene expression, e.g. in a mammalian host cell. For example, the antagonist may bind to the target RNA by hybridizing thereto. Further, the antagonist may be capable of causing instability, cleavage and/or degradation of the bacterial target RNA. In a preferred embodiment, the antagonist is a nucleic acid effector molecule capable of hybridizing to the bacterial target RNA or a precursor thereof. A further suitable class of antagonists is aptamers, which may be obtained by a selection procedure (SELEX) for nucleic acid based test compounds which bind to the target RNA molecule. Still a further class of antagonists is antibodies or antibody fragments or related molecules, which may be obtained by known immunisation protocols. Further antagonists may be selected from peptidic compounds or non-peptidic organic compounds, e.g. low molecular weight compounds (i.e. compounds having a molecular weight of 2500 or less) capable of interacting with the bacterial target RNA molecule. Furthermore, the antagonists may comprise covalently or non-covalently linked combinations of molecules, e.g. combinations of sequence-complementary nucleic acid effector molecules and aptamers. In a preferred embodiment of the invention, the antagonist is selected from nucleic acid effector molecules as described in detail below.

The nucleic acid effector molecule may be selected from antisense molecules, i.e. a single-stranded nucleic acid molecules having a sufficient degree of identity with the target sequence in order to hybridize therewith and thus cause a reduction of gene expression. The antisense-molecules may be RNA or DNA molecules or nucleic acid analogs as described in detail below. The length of the antisense molecule is preferably at least 12, more preferably at least 15 nucleotides and up to 150, more preferably up to 120 nucleotides.

A further class of nucleic acid effector molecules are ribozymes, i.e. RNA molecules or analogs thereof as described below capable of enzymatically cleaving RNA molecules at certain positions. Ribozymes may be selected from hammerhead ribozymes, hairpin ribozymes, hepatitis delta virus ribozymes, and other including artificially constructed ribozymes as known in the art.

A still further class of preferred nucleic acid molecules are capable of RNA interference, e.g. siRNA molecules, i.e. double-stranded RNA or RNA analog molecules, wherein each RNA strand preferably has a length from 15 to 28 nucleotides, and wherein at least one strand may have a 3' overhang from 1-5, e.g. 1 to 3 nucleotides. A further example of RNA interference molecules are small hairpin (sh)RNA molecules, i.e. single-stranded self-complementary RNA or RNA analog molecules capable of forming a hairpin which may also effect RNA interference.

Further, the invention refers to precursors of the above effector molecules, i.e. long RNA molecules or RNA analog molecules which may processed, e.g. within the organism, to give the active effector molecule. Also encompassed by the present invention is the use of DNA molecules encoding the effector molecules or precursors thereof in operative linkage to a functional expression control sequence. These DNA molecules may be expressed in the host in order to provide the active effector molecules or the precursors thereof.

The nucleic acid effector molecules may be selected from nucleic acid molecules comprising ribonucleotide and/or deoxyribonucleotide building blocks and/or nucleotide analog building blocks, e.g. sugar-, backbone-, or nucleobase-modified ribonucleotides. In preferred sugar-modified ribonucleotides, the 2'-OH group is replaced by a group selected from H, OR, R, halo, SH, SR, $NH_2$, NHR, $NR_2$, CN, or a bridge connecting the 2' and 4' carbons resulting in locked nucleic acids (LNA), wherein R is $C_1$-$C_6$ alkyl, $C_2$-$C_6$ alkenyl or alkynyl and halo is F, Cl, Br or I. In preferred backbone-modified ribonucleotides, the phosphoester group connecting to adjacent ribonucleotides may be replaced by a modified group, e.g. a phosphothioate group, a methylphosphonate group, a borane phosphonate, and a 3'-O-phosphopropylamino group. In preferred nucleobase-modified ribonucleotides, nucleotides containing a non-naturally occurring nucleobase instead of a naturally occurring nucleobase may be used. The ribose may also be substituted by a morpholino ring and the sugar-phosphodiester backbone may be replaced by a peptide backbone resulting in a peptide nucleic acid. It should be noted that the above modifications may be combined. Further possible modifications are lipid residues, cholesterol residues, or fluorophors.

The nucleic acid effector molecules of the present invention have to have a sufficient identity to the bacterial target RNA molecule in order to mediate target-specific reduction of a gene expression, e.g. by RNA interference or other mechanisms. Preferably the identity to the bacterial target RNA is at least 70%, more preferably at least 80%, even more preferably at least 90% and up to 100% over a length of preferably at least 15 and more preferably at least 20 nucleotides.

Nucleic acid effector molecules may be provided as:
(i) a naked nucleic acid,
(ii) a non-viral vector including liposomes, cationic lipids, polyethylenimine, poly-L-lysine or other non-viral compounds suitable for gene delivery,
(iii) a viral vector including AAV vectors, adenoviral vectors, lentiviral vectors, retroviral vectors, herpes viral vectors or other viral vectors suitable for gene delivery, or
(iv) a bacterial vector including invasive or intracellular bacterial vectors e.g. based on *E. coli, Salmonella* species, *Listeria monocytogenes, Mycobacteria* vectors.

Still a further aspect of the present invention is a pharmaceutical composition comprising as an active agent an antagonist, e.g. a nucleic acid effector molecule as described above together with a pharmaceutically acceptable carrier. The composition may be used for diagnostic and/or therapeutic applications in human medicine or in veterinary medicine.

For diagnostic or therapeutic applications, the compositions may be in form of a solution, e.g. an injectable solution, a cream, ointment, tablet, suspension or the like. The composition may be administered in any suitable way, e.g. by injection, by oral, topical, nasal, pulmonal, rectal application etc. The carrier may be any suitable pharmaceutical carrier. Preferably, a carrier is used, which is capable of increasing the efficacy of nucleic acid effector molecules to enter the target cells. Suitable examples of such carriers are lipids, liposomes, particularly cationic liposomes. Further examples of carriers are nano-particles including biodegradable and ferromagnetic nano-particles, the later of which can be navigated by magnetic forces, viral vectors including viral and virus-like particles derived from adeno-associated virus particles, adenovirus particles, retroviral particles, lentiviral particles, herpes virus particles and particles derived from other viruses suitable as gene carriers, or bacterial vectors as described above. Further, the antagonist may be covalently or non-covalently linked to a targeting moiety, e.g. a bacterial delivery peptide.

A further embodiment of the present invention refers to the use of the bacterial target RNA or an miRNA molecule derived therefrom as a therapeutic or diagnostic agent. Suitable miRNA molecules are preferably single-stranded RNA molecules having a length of 15-28, e.g. 16-23, nucleotides, optionally comprising nucleic acid analogue building blocks as described above. Suitable miRNA molecules derived from the miRNA precursor-like structure from the mycobacterial tuf mRNA are described in detail below (cf. FIG. 6). The bacterial RNA or mRNA molecules derived therefrom may be used, e.g. as decoys for therapeutic uses or as marker for diagnostic uses.

Still a further aspect of the invention refers to a screening method for identifying and/or characterizing novel compounds which act as antagonists against a bacterial target RNA as described above. The screening assay may be carried out as a cellular assay or a cell-free assay. Preferably, the screening assay comprises contacting a test compound, e.g. a low molecular weight compound, a peptide or polypeptide, a non-peptidic organic compound, a nucleic acid molecule, etc., with a target RNA or a precursor thereof, and determining the presence or absence of interactions between the test compound and the target RNA.

Moreover, the present invention is illustrated by the following figures and examples:

FIGURES

FIG. 1: Computer-based identification algorithm (RNA base pair matrix, shift width 1 nt) of miRNA analogous structures having a pre-determined length of 140 nt by self-alignment. The intramolecular self-complementarity is expressed by continuous lines consisting of individual dots.

Figure 2:
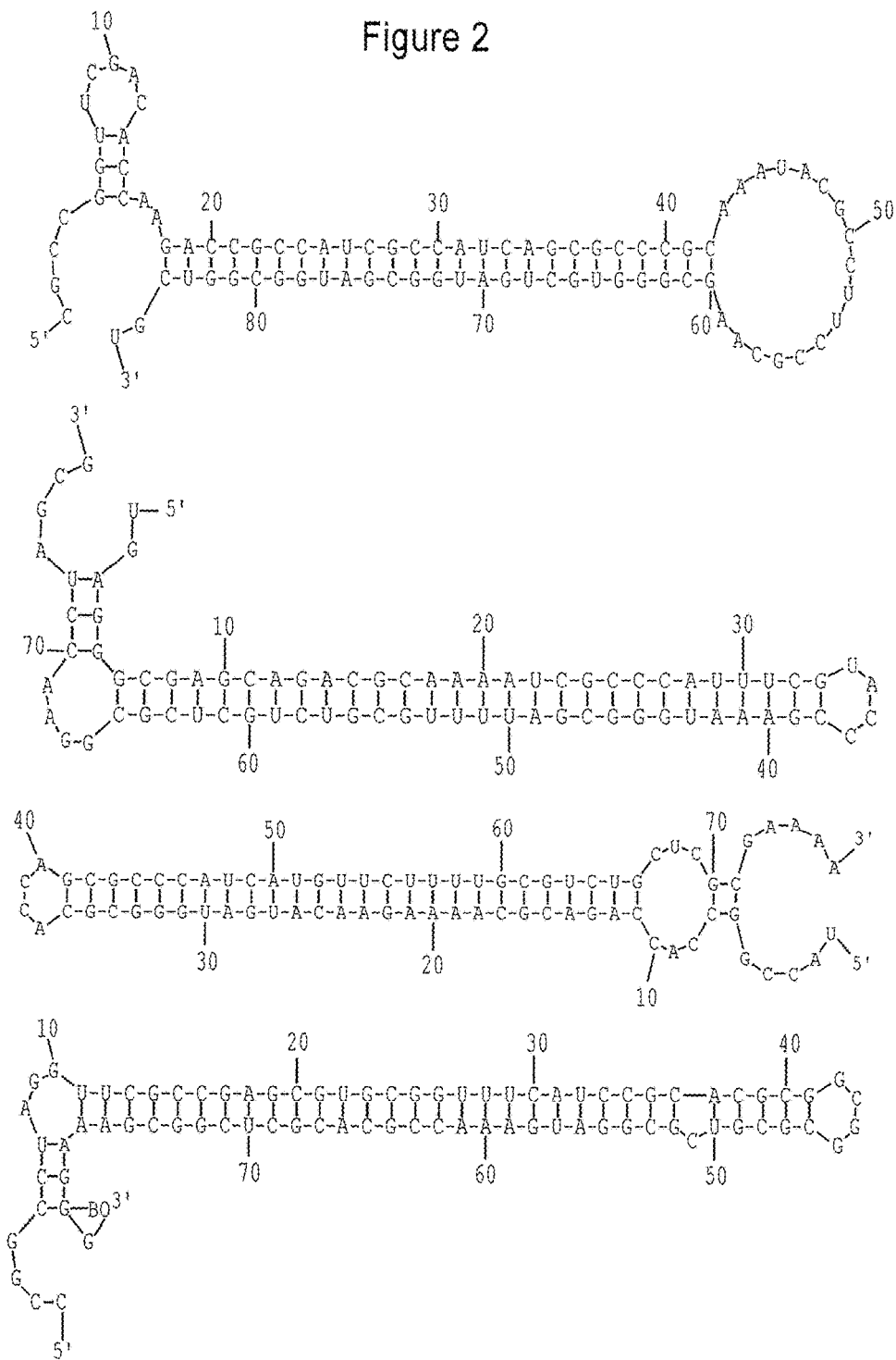

FIG. 2: Examples of miRNA analogous structures derived from *M. tuberculosis* sequences (SEQ ID NO: 1, 2, 3 & 4).

Figure 3:
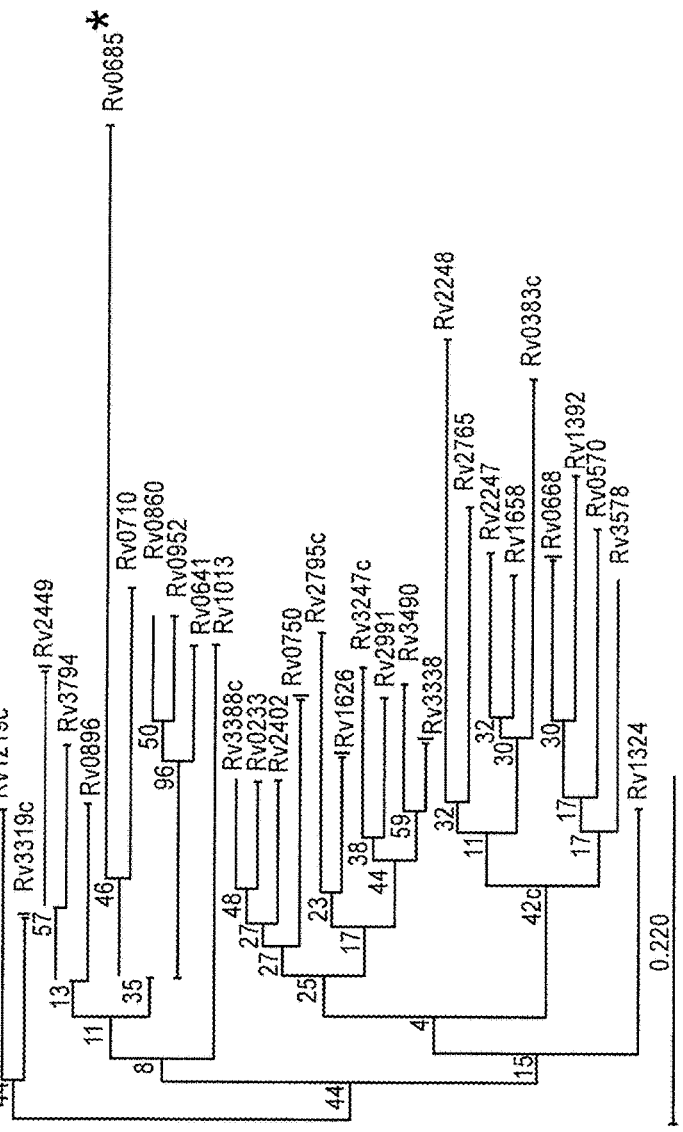

FIG. 3: Sequence conservation within the miRNA analogous structures from *M. tuberculosis*. a) Alignment tree of all miRNA candidates of *M. tuberculosis*. b) Portion of the sequence alignment. *This structure differs from other structure sequences by being homologous to two human sequences (SEQ ID NO: 5, 6, 7, 8, 9 & 10).

Figure 4:
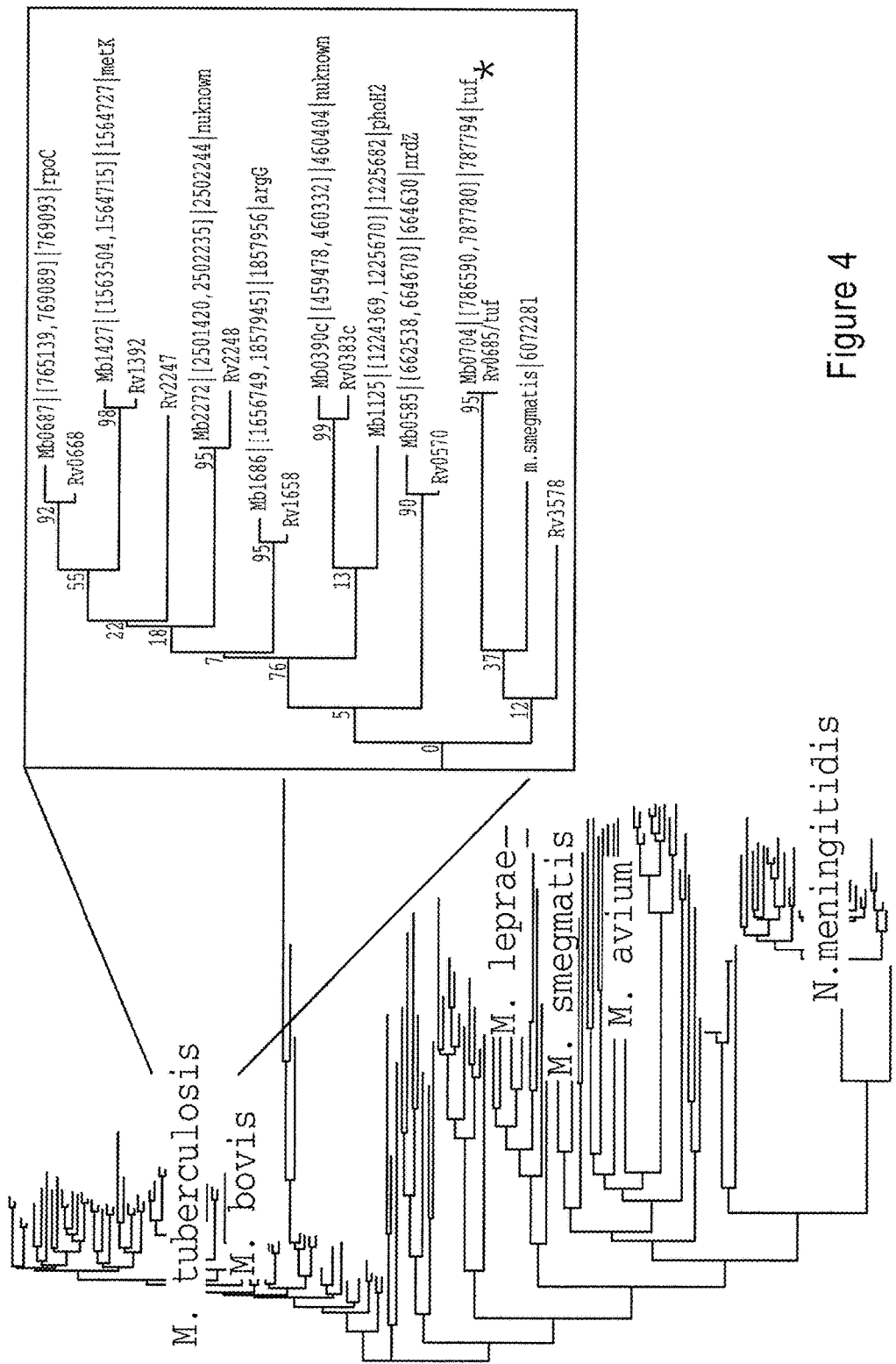

FIG. 4: Sequence conservation within miRNA analogous structures from different Bacteria. *miRNA analogous structure with homology to human MHC-II and Myelin P0 is absolutely conserved among the tuf genes of *M. tuberculosis* and *M. bovis* and partly conserved in *M. smegmatis*. It does not occur in any of the other investigated organisms.

FIG. 5: Predicted structure of the miRNA analogous structure having homology to human sequences as shown in FIGS. 3 and 4, and a simplified schematic depiction of this structure (SEQ ID NO: 3).

FIG. 6: Sequences, structures (dot-bracket depiction) and folding energies of potential mature miRNA molecules (ranging from 23-mere to 16-mere) which may be obtained by processing from the stem of the precursor structure shown in FIG. 5. a) 23-mere (residues 11-33, 12-34, 13-35, and 14-36 of SEQ ID NO: 3), 22-mere (residues 11-32, 12-33, 13-34, 14-35, and 15-36 of SEQ ID NO: 3), 21-mere (residues 11-31, 12-32, 13-33, 14-34, 15-35, and 16-36 of SEQ ID NO: 3), 20-mere (residues 11-30, 12-31, 13-32, 14-33, 15-34, 16-35, and 17-36 of SEQ ID NO: 3), 19-mere (residues 11-29, 12-30, 13-31, 14-32, 15-33, 16-34, 17-35, and 18-36 of SEQ ID NO: 3), 18-mere (residues 11-28, 12-29, 13-30, 14-31, 15-32, 16-33, 17-34, 18-35, and 19-36 of SEQ ID NO: 3), 17-mere (residues 11-27, 12-28, 13-29, 14-30, 15-31, 16-32, 17-33, 18-34, 19-35, and 20-36 of SEQ ID NO: 3), and 16-mere (residues 11-26, 12-27, 13-28, 14-29, 15-30, 16-31, 17-32, 18-33, 19-34, 20-35, and 21-36 of SEQ ID NO: 3) processed from 5' terminal stem. b) 23-mere (residues 41-63, 42-64, 43-65, and 44-66 of SEQ ID NO: 3) 22-mere (residues 41-62, 42-63, 43-64, 44-65, and 45-66 of SEQ ID NO: 3), 21-mere (residues 41-61, 42-62, 43-63, 44-64, 45-65, and 46-66 of SEQ ID NO: 3), 20-mere (residues 41-60, 42-61, 43-62, 44-63, 45-64, 46-65, and 47-66 of SEQ ID NO: 3), 19-mere (residues 41-59, 42-60, 43-61, 44-62, 45-63, 46-64, 47-65, and 48-66 of SEQ ID NO: 3), 18-mere (residues 41-58, 42-59, 43-60, 44-61, 45-62, 46-63, 47-64, 48-65, and 49-66 of SEQ ID NO: 3), 17-mere (residues 41-57, 42-58, 43-59, 44-60, 45-61, 46-62, 47-63, 48-64, 49-65, and 50-66 of SEQ ID NO: 3), and 16-mere (residues 41-56, 42-57, 43-58, 44-59, 45-60, 46-61, 47-62, 48-63, 49-64, 50-65, and 51-66 of SEQ ID NO: 3) processed from 3' terminal stem.

Figure 7:
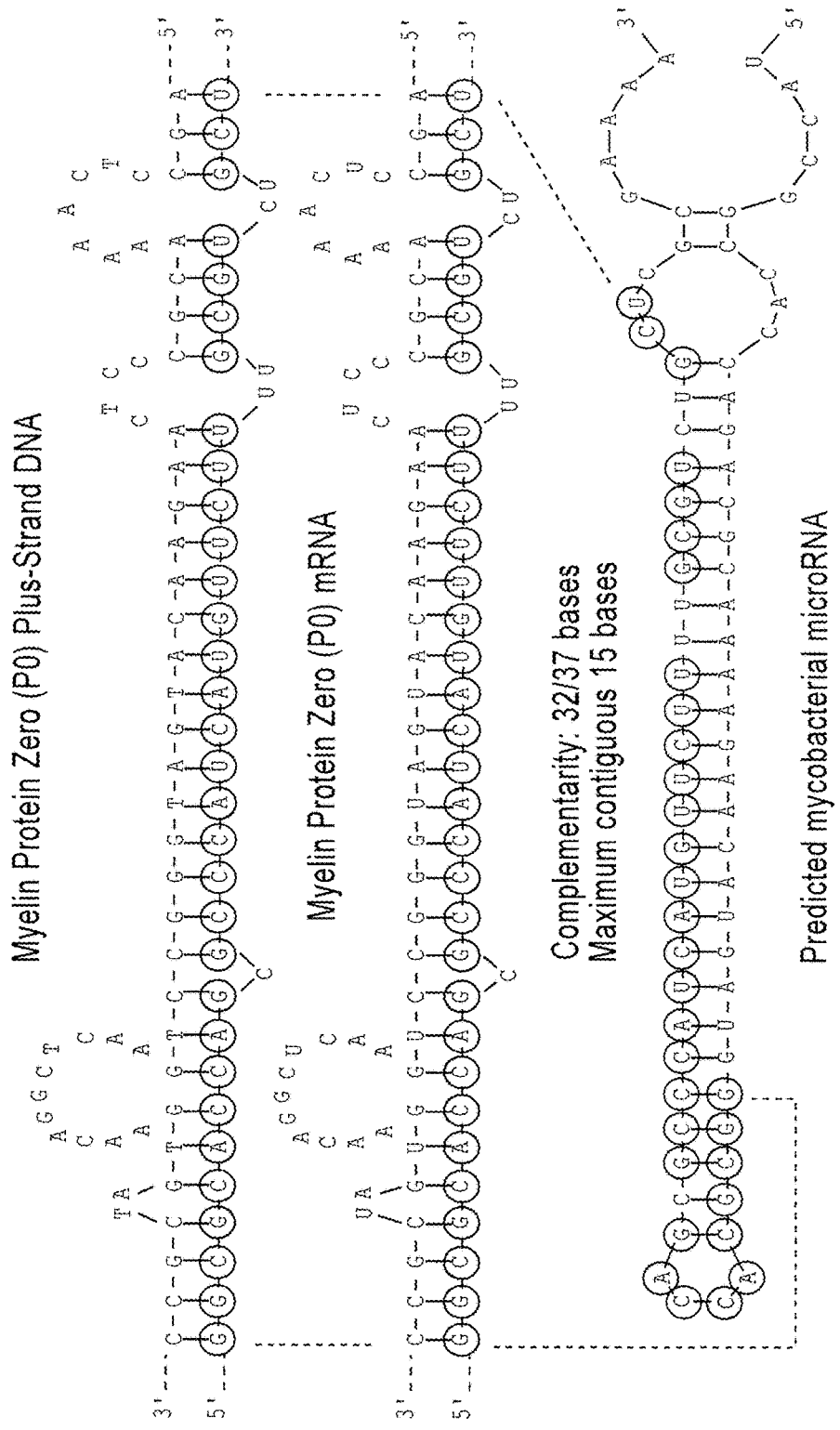

FIG. 7: Homology between the bacterial miRNA target sequence (SEQ ID NO: 3) and potential human host sequences. The sequence homology to the myelin P0 mRNA (SEQ ID NO: 17 and residues 32-68 of SEQ ID NO: 3) and to the plus strand of the myelin P0 gene (SEQ ID NO: 16 and residues 32-68 of SEQ ID NO: 3) is shown.

Figure 8:
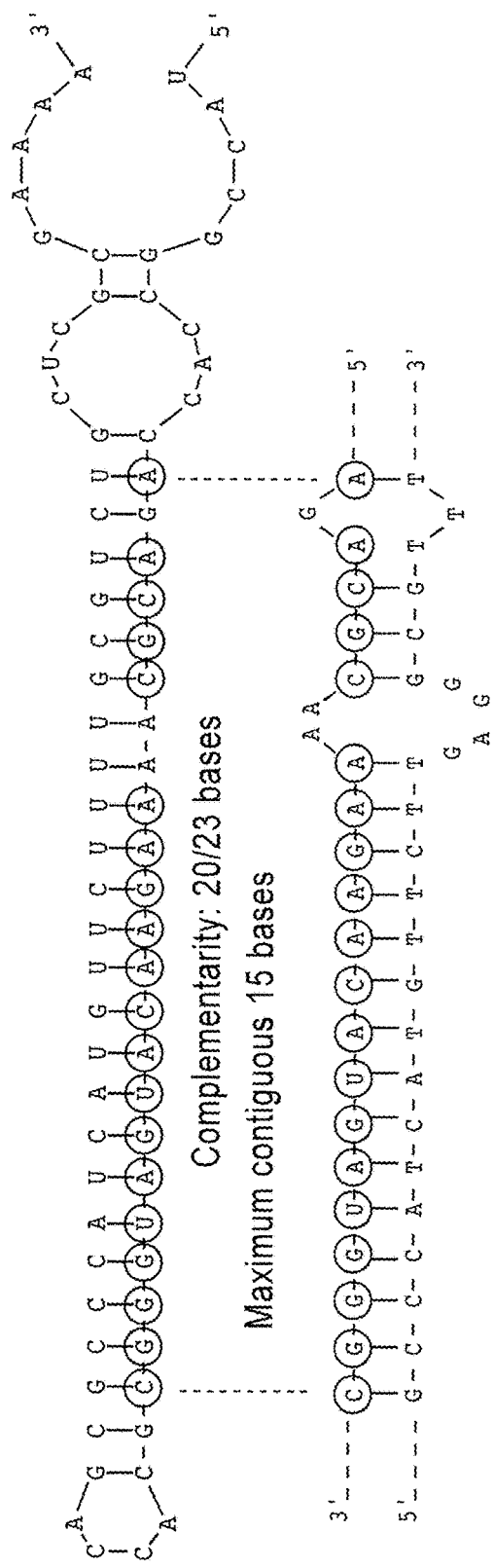

FIG. 8: Homology between the bacterial mRNA target sequence (SEQ ID NO: 3) and human host sequences. Homology to the minus strand of the myelin P0 gene (SEQ ID NO: 11 and residues 12-34 of SEQ ID NO: 3).

Figure 9:
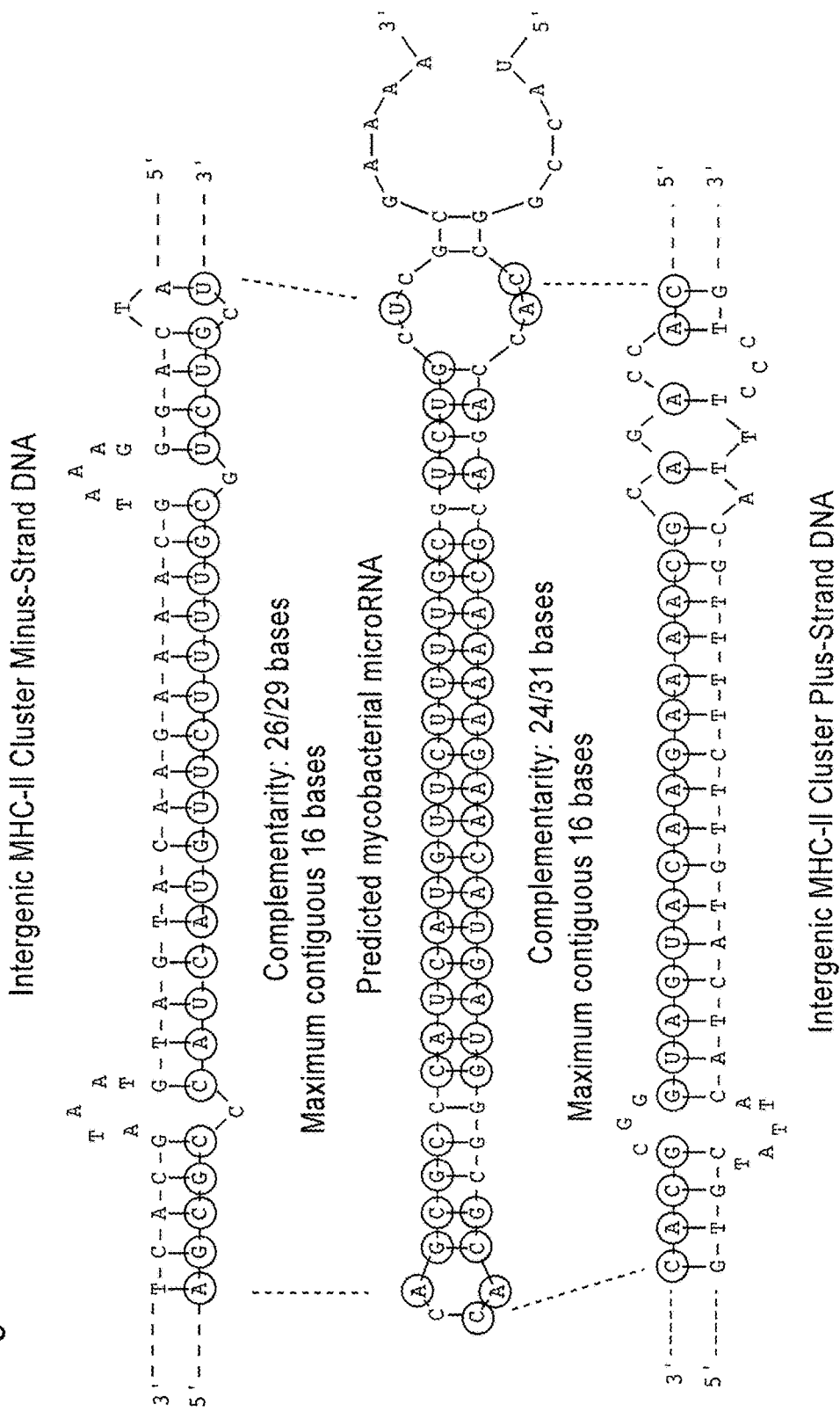

FIG. 9: Homology between the bacterial target miRNA sequence (SEQ ID NO: 3) and human host sequences. Homology to the plus strand DNA (SEQ ID NO: 13 and residues 8-38 of SEQ ID NO: 3) and minus strand DNA (SEQ ID NO: 12 and residues 40-68 of SEQ ID NO: 3) of the MHC-II cluster between the two MHC-II subunits HLA-DRB7 and HLA-DRB8.

Figure 10:
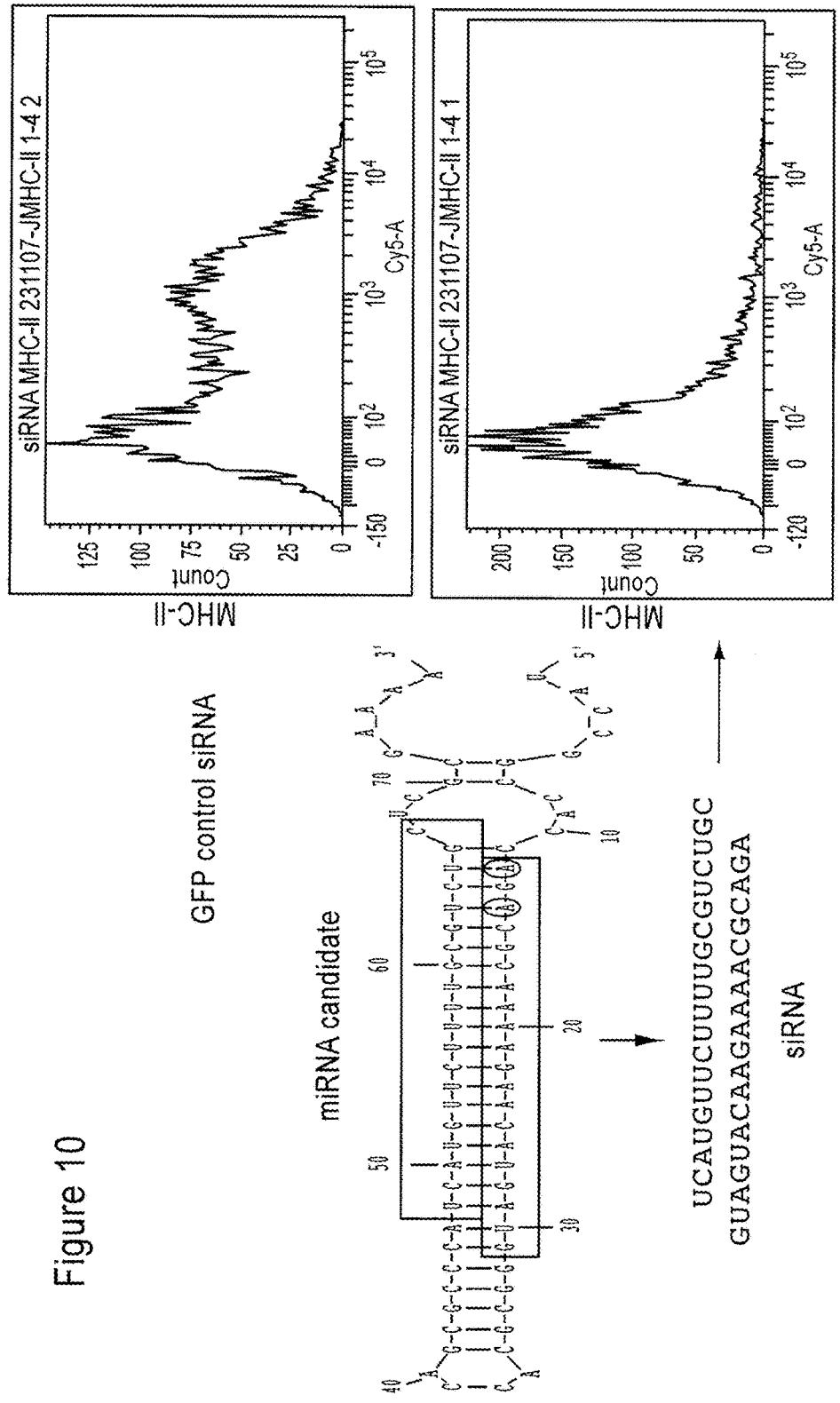

FIG. 10: Specific MHC-II inhibition in primary human monocytes by an miRNA candidate-derived siRNA. Monocytes were isolated from a buffy coat, transfected with chemically synthesized siRNAs using nucleofection prior to IFN-γ stimulation. MHC-II expression was detected by FACS analysis 24 h after transfection. Upper panel: GFP-directed control siRNA; lower panel: miRNA candidate-derived MHC-II-specific siRNA (SEQ ID NO: 3, 14 & 15).

Figure 11:
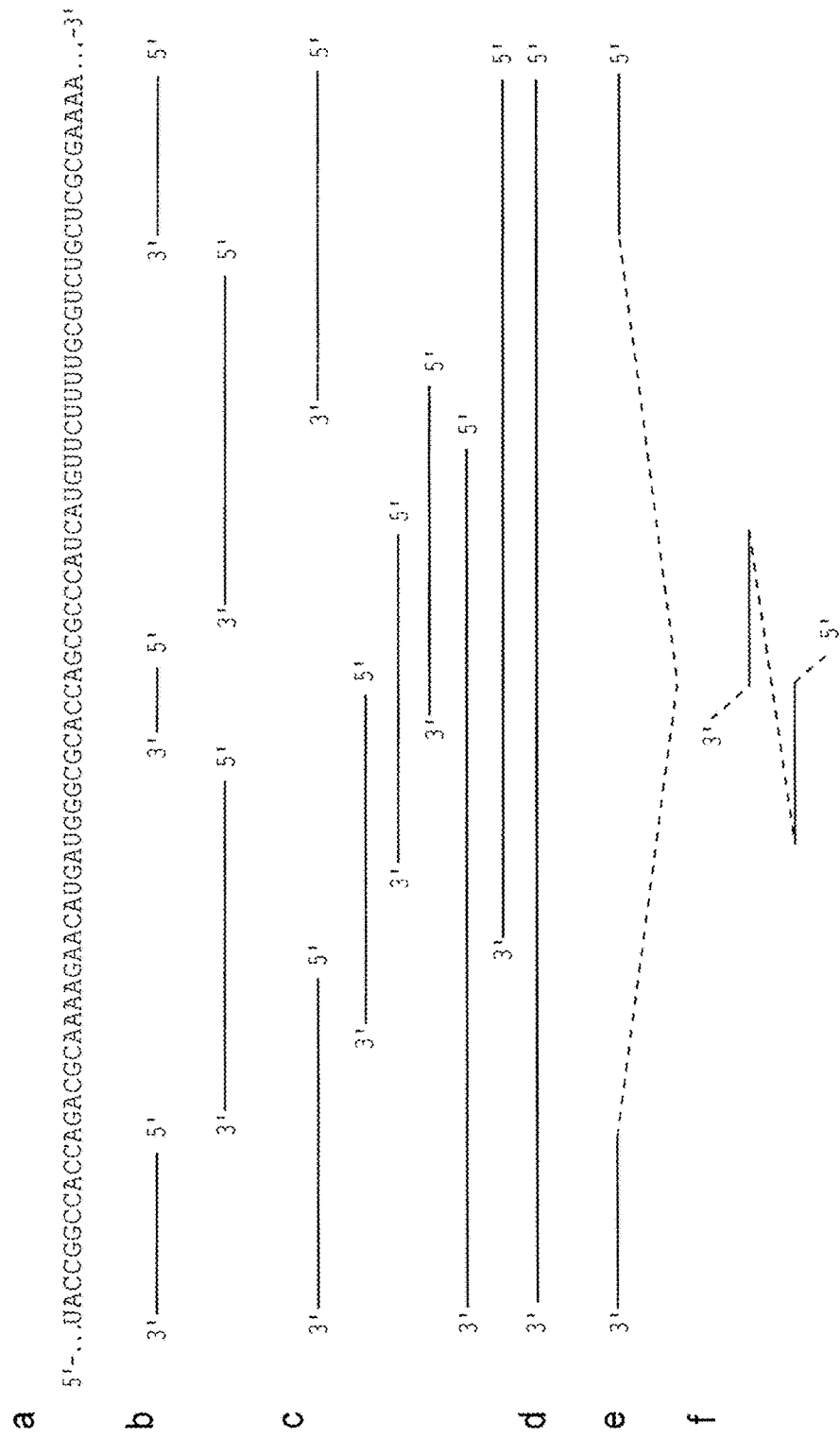
Figure 12:
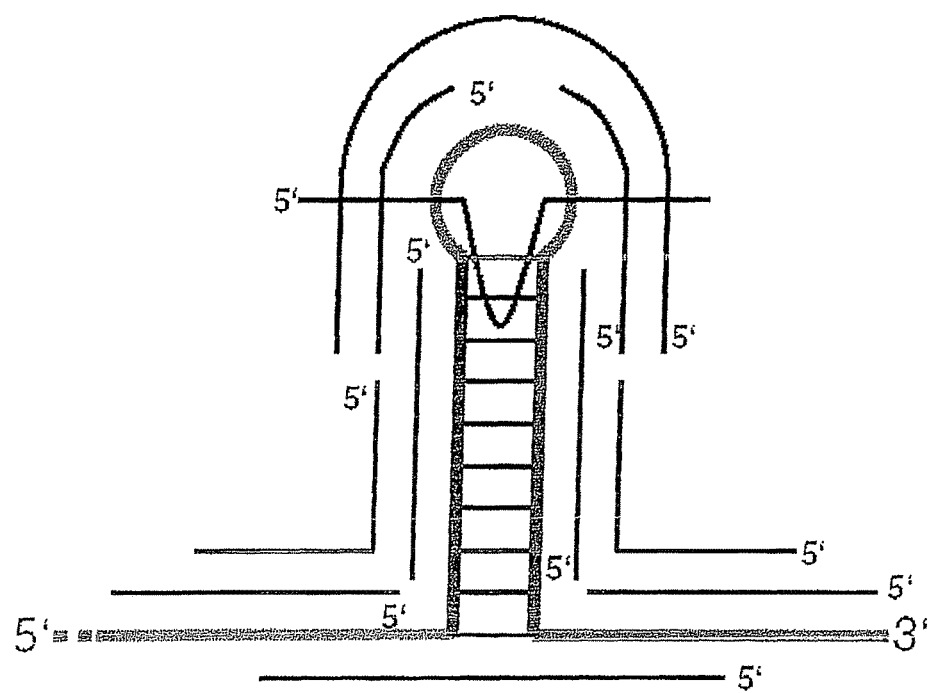

FIG. 11: Examples for the positioning of nucleic acid based antagonists with regard to the sequence of the identified bacterial target RNA (a). b) positioning against unpaired regions, e.g. the 5' terminal sequence, the loop and the 3' terminal sequence, or positioning against portions of the paired stem region. c) Positioning against two, three or several of the regions described under b). d) Positioning against the whole sequence from a). e) Positioning against discontinuous sequences, i.e. both free ends excluding the hairpin (stem loop) structure. f) Positioning against discontinuous sequences from the hairpin structure (SEQ ID NO: 3).

FIG. 12: Examples for the positioning of nucleic based antagonists relative to the structure of an identified bacterial target RNA. Positioning against unpaired areas such as the 5' terminus, the loop and the 3' terminus of the sequence or against portions of the paired stem regions. Further positionings are directed against two, three or more of these structural elements or against the whole sequence. Further antagonists may be directed against discontinuous portions of the target structure, e.g. against both free ends or the hairpin region.

FIG. 13: Specific examples of nucleic acid based antagonists directed against the identified bacterial mycobacterial target RNA (a). b) Oligodesoxyribonucleotide which is preferably directed with its 3' end against an unpaired of the portion of the target sequence. c) Ribozyme directed against a target sequence GUH (wherein H is any base except G). d)

Antisense RNA which preferably has a length between 70 and 120 nucleotides and a structure with free 5' and 3' termini. e) siRNA molecule having a sense and an antisense strand and two nt 3' overhangs. Preferably, the guide strand of the siRNA is not capable of intramolecular folding or has a positive free Gibbs folding energy. f) shRNA molecules including the guide structure from e) (SEQ ID NO: 3, 18, 19, 20, 21, 22, 23 & 24).

EXAMPLE

1. Identification of miRNA Analogous Structures in Bacteria

By means of bioinformatic analysis on the basis of self-complementarity and length (FIG. 1) miRNA-analogous RNA secondary structures were identified in the transcriptome of *M. tuberculosis* (FIG. 2) (SEQ ID NO: 1, 2, 3 & 4). Next, the conservation of the identified RNA structures was analysed (FIG. 3). It was found that the sequences exhibit a very high homology within the stem region of the hairpin structure and have a variability in the loop region. Noteworthy is a sequence, which does not show any homology in the middle sequence portion including the loop region to the other sequences (FIG. 3b) (SEQ ID NO: 5, 6, 7, 8, 9 & 10).

This sequence is a transcribed sequence from the tuf gene of *M. tuberculosis* and *M. bovis* including *M. bovis* BCG and exhibits some homology to a sequence from *M. smegmatis* (FIGS. 3 and 4) (SEQ ID NO: 5, 6, 7, 8, 9 & 10). It exhibits at its 3' terminus a hairpin structure characteristic for miRNA molecules (FIG. 5) (SEQ ID NO: 3). Further, the hairpin structure exhibits a high degree of homology to human host sequences sufficient for RNA interference (FIGS. 7-9) (SEQ ID NO: 11, 12, 13, 16 & 17 and residues 12-34, 8-38, 40-68 and 32-68 of SEQ ID NO: 3).

The sequence portions homologous to human host sequences fulfil the criteria of preferred active guide sequences in antisense sRNA or mature miRNA molecules (FIG. 6) (residues 11-33, 12-34, 13-35, 14-36, 11-32, 12-33, 13-34, 14-35, 15-36, 11-31, 12-32, 13-33, 14-34, 15-35, 16-36, 11-30, 12-31, 13-32, 14-33, 15-34, 16-35, 17-36, 11-29, 12-30, 13-31, 14-32, 15-33, 16-34, 17-35, 18-36, 11-28, 12-29, 13-30, 14-31, 15-32, 16-33, 17-34, 18-35, 19-36, 11-27, 12-28, 13-29, 14-30, 15-31, 16-32, 17-33, 18-34, 19-35, 20-36, 11-26, 12-27, 13-28, 14-29, 15-30, 16-31, 17-32, 18-33, 19-34, 20-35, 21-36, 41-63, 42-64, 43-65, 44-66, 41-62, 42-63, 43-64, 44-65, 45-66, 41-61, 42-62, 43-63, 44-64, 45-65, 46-66, 41-60, 42-61, 43-62, 44-63, 45-64, 46-65, 47-66, 41-59, 42-60, 43-61, 44-62, 45-63, 46-64, 47-65, 48-66, 41-58, 42-59, 43-60, 44-61, 45-62, 46-63, 47-64, 48-65, 49-66, 41-57, 42-58, 43-59, 44-60, 45-61, 46-62, 47-63, 48-64, 49-65, 50-66, 41-56, 42-57, 43-58, 44-59, 45-60, 46-61, 47-62, 48-63, 49-64, 50-65, and 51-66 of SEQ ID NO: 3). This means that these sequence portions substantially have positive or only slightly negative folding energies and/or comprise long free termini (cf. Ref. 1). This criterion is particularly fulfilled by the shorter hypothetic guide sequences and preferably by those derived from the 5' terminal portion of the stem (FIG. 6a).

The expression of the tuf mRNA is known (cf. Ref. 2), it is differentially expressed following bacterial phagocytosis (cf. Ref. 3), and the 3'-terminal hairpin structure is known to function as atypical transcriptional terminator (cf. Ref. 4). However, unknown is the high homology of the stem region of the 3'-terminal hairpin structure (SEQ ID NO: 3) to human sequences. These host sequences are the 3'UTR of the myelin P0 mRNA (SEQ ID NO: 17) or the corresponding sequences of the myelin P0 gene (SEQ ID NO: 11 & 16) and a non-transcribed region in the MHC-II cluster between both MHC-II subunits HLA-DRB7 and HLA-DRB8 (SEQ ID NO: 12 & 13).

The homologous region to the myelin P0 mRNA (SEQ ID NO: 17) and to the plus strand of the myelin P0 gene (SEQ ID NO: 16) comprises 32 bases in a 37 base long homologous region having a maximum of 15 contiguous complementary bases (32/37/15) (FIG. 7) (residues 32-68 of SEQ ID NO: 3). The homology to the minus strand of the myelin P0 gene (SEQ ID NO: 11) comprises 20/23/15 bases (FIG. 8) (residues 12-34 SEQ ID NO:3). The homology to the plus strand of the DNA of the MHC-II cluster comprises 24/31/16 bases (SEQ ID NO: 12 and residues 8-38 of SEQ ID NO: 3) and to the minus strand DNA 26/29/16 bases (SEQ ID NO: 13 and residues 40-68 of SEQ ID NO: 3) (FIG. 9).

MHC-II expression is down-regulated in human cells in the course of infection with *M. tuberculosis* (Refs. 5 and 6). The molecular mechanisms of this down-regulation is unknown, although, the lipoprotein LprG of *M. tuberculosis* is known to be able to inhibit the MHC-II dependent antigen presentation in human macrophages (Ref. 7). It is assumed, that the identified bacterial target RNAs alone or together with LprG might play a role in MHC-II down-regulation. A sRNA derived from the miRNA candidate with high homology to the intergenic region between MHC-II subunits HLA-DRB7 and HLA-DRB8 was able to efficiently inhibit MHC-II expression in IFN-γ stimulated primary human monocytes as shown in FIG. 10. (SEQ ID NO: 3, 21 & 22). Further, 20-30% of all tuberculosis incidents also inflict the central nervous system (CNS). In this process, the interference of a bacterial mRNA with the myelin P0 gene might play a role. (SEQ ID NO: 3, 11, 16 & 17).

2. Development of Nucleic Acid Based Antagonists

The interference of any bacterial target sequence, e.g. a tuf mRNA derived miRNA analogous structure, but not limited thereto, with corresponding host sequences can be reduced and/or inhibited by nucleic acid effector molecules. These nucleic effector molecules may be directed against the identified bacterial miRNA analogous sequences or precursors thereof, e.g. the complete tuf mRNA which comprises the hairpin structure at its 3' terminus within or without the miRNA analogous sequence regions.

The therapeutic efficacy of the novel nucleic acid based antagonists is achieved by functional blocking and/or cleavage of the bacterial target sequences or precursors thereof. Further, the antagonists are suitable for diagnostic applications, particularly in order to identify the bacterial target sequences as biomarkers for the stage and the course of a bacterial infection.

The antagonists may be directed against any region of the bacterial target sequence, preferably a region having a length of at least 15 nucleotides (FIG. 11). (SEQ ID NO: 3). The target regions comprise the 3' or 5' termini, the stem region, the hairpin, and the regions between these structural elements. Further, the antagonists may be directed against specific structural element, e.g. against both free termini without the hairpin structure or the 5' and 3' terminal loop bases adjacent to the hairpin without the bases in the centre of the loop structure and portions of the stem region (FIG. 12).

In FIG. 13, specific embodiments are shown:

An antisense oligodesoxyribonucleotide preferably directed with its 3' end against an accessible (unpaired) region of the target sequence (SEQ ID NO: 18), a hammerhead ribozyme directed against a GUH sequence (wherein H is any base except G) (SEQ ID NO: 19), an antisense RNA molecule which preferably has a length between 70 and 120 nucleotides and which comprises free (accessible) 5' and 3' ends (SEQ ID NO: 20), or an siRNA molecule, the guide strand of which preferably is not capable of intramolecular folding (SEQ ID NO: 21 & 22) or two shRNA molecules derived therefrom in which the antisense strand can be upstream or downstream of the sense strand. (SEQ ID NO: 23 & 24).

Figure 13:
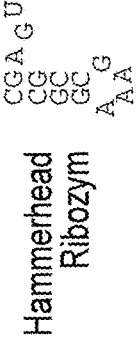

It should be noted that that the nucleic acid based antagonists shown in FIG. 13 are only exemplary embodiments of the present invention without limiting its scope. For example, the nucleic acid based antagonists may also be directed to portions of the tuf mRNA (or any other bacterial RNA), which are located outside the miRNA analogous structure at the 3' terminus of the tuf mRNA.

REFERENCES

1. Patzel, V., Rutz, S., Dietrich, I., Koberle, C., Scheffold, A., Kaufmann, S. H. E. (2005). Design of siRNAs producing unstructured guide-RNAs results in improved RNA interference efficiency. *Nature Biotechnology* 23(11), 1440-1444.
2. Carlin, N. I., Löfdahl, S., Magnusson M. (1992). Monoclonal antibodies specific for elongation factor Tu and complete nucleotide sequence of the tuf gene in *Mycobacterieum tuberculosis*. Infect. Immun. 60, 3136-3142.
3. Monahan, I. M., Betts, J., Banerjee, D. K., and Butcher, P. D. (2001). Differential expression of mycobacterial proteins following phagocytosis by macrophages. *Microbiology.* 147, 459-471.
4. Unniraman, S., Prakash, R., and Nagaraja, V. (2001). Alternate paradigm for intrinsic transcription termination in eubacteria. *J Biol. Chem.* 276, 41850-41855.
5. Gercken, J., Pryjma, J., Ernst, M., Flad, H-D. (1994). Defective antigen presentation by *Mycobacterium tuberculosis*-infected monocytes. Infect. Immun. 62, 3472-3478.
6. Noss, E. H., Harding, C. V., and Boom, W. H. (2000). *Mycobacterium tuberculosis* inhibits MHC class II antigen processing in murine bone marrow macrophages. Cell Immunol. 201, 63-74.
7. Gehring, A. J., Dobos, K. M., Belisle, J. T., Harding, C. V., and Bloom, W. H. (2004). *Mycobacterium tuberculosis* LprG (Rv1411c): A novel TLR-2 ligand that inhibits human macrophage class II MHC antigen processing. J. Immunol. 173, 2660-2668.

The invention claimed is:

1. An isolated antagonist directed against a bacterial RNA or a precursor thereof, wherein the bacterial RNA is homologous or complementary to RNA or DNA host sequences and/or innate bacterial sequences, coupled with or enclosed by a pharmaceutical carrier which increases the efficacy of the antagonist to enter target cells, wherein said antagonist is a nucleic acid effector molecule selected from
   (i) antisense molecules, ribozymes, siRNA molecules, and shRNA molecules
   (ii) precursors of the molecules from (i) and
   (iii) DNA molecules encoding the molecules from (i) and (ii).

2. The isolated antagonist of claim 1 directed against a bacterial RNA or a precursor thereof, wherein the bacterial RNA is a contiguous bacterial RNA stretch that has a length of at least 10 nucleotides.

3. The isolated antagonist of claim 1 directed against a bacterial RNA or a precursor thereof, wherein the bacterial RNA that is homologous or complementary to RNA or DNA host sequences and/or innate bacterial sequences has a length of at least 15 nucleotides, and wherein the degree of homology or complementarity is at least 75%.

4. The isolated antagonist of claim 1 directed against a bacterial RNA or a precursor thereof, wherein the bacterial RNA has a stem-loop secondary structure.

5. The isolated antagonist of claim 1 directed against a bacterial RNA or a precursor thereof, wherein the bacterial RNA is from mycobacteria.

6. The isolated antagonist of claim 1 directed against a bacterial RNA or a precursor thereof, wherein the bacterial RNA is from the mycobacterial tuf gene.

7. The isolated antagonist of claim 1, wherein said carrier is suitable for the treatment of bacterial infections.

8. The isolated antagonist of claim 1 which is present as:
   (i) a naked nucleic acid,
   (ii) a non-viral vector including liposomes, cationic lipids, polyethylenimine, poly-L-lysine or other non-viral compounds suitable for gene delivery,
   (iii) a viral vector suitable for gene delivery, or
   (iv) a bacterial vector including invasive or intracellular bacterial vectors.

9. The isolated antagonist of claim 1, wherein said antagonist is coupled to ferromagnetic nanoparticles.

10. The isolated antagonist of claim 1 which is covalently or non-covalently linked to a targeting moiety.

11. A pharmaceutical composition comprising more than one antagonist of claim 1 together with said pharmaceutically acceptable carrier which increases the efficacy of the antagonist to enter target cells, wherein said carrier is selected from the group consisting of lipids, liposomes, ferromagnetic nano-particles, viral vectors, bacterial vectors and gene carriers.

12. The isolated antagonist according to claim 1, where said antagonist is a nucleic acid molecule with at least one sugar, backbone or nucleobase modified ribonucleotide.

13. The isolated antagonist according to claim 1, where said antagonist is a nucleic acid effector molecule which is modified with lipid residues, cholesterol residues or florophors.

14. The isolated antagonist according to claim 1, wherein said pharmaceutical carrier is selected from the group consisting of lipids, liposomes, ferromagnetic nano-particles, viral vectors, bacterial vectors and gene carriers.

15. The isolated antagonist of claim 1, wherein said antagonist is directed against bacterial mRNA from a portion of the mycobacterial tuf gene comprising the sequence according to SEQ ID NO: 3.

16. The isolated antagonist according to claim 2, wherein the bacterial RNA is from *M. tuberculosis*.

17. The isolated antagonist according to claim 10, wherein said targeting moiety is a bacterial delivery peptide.

18. The isolated antagonist of claim 7, wherein the bacterial infections are caused by or associated with intracellular bacteria.

19. The isolated antagonist of claim 7 wherein said carrier is suitable for the treatment of mycobacterial infections.

20. The isolated antagonist of claim 19, wherein the mycobacterial infections are caused by and/or associated with *M. tuberculosis*.

21. The isolated antagonist of claim 8, wherein said bacterial vector is based on a bacteria selected from the group consisting of *E. coli, Salmonella* species, *Listeria monocytogenes*, and Mycobacteria.

22. The isolated antagonist of claim 4, wherein the stem has a length of at least 15 base pairs.

23. The isolated antagonist of claim 22, wherein the stem has a length of at least 20 base pairs.

24. The isolated antagonist of claim 4 wherein the stem has a degree of self-complementarity within the stem of at least 70%.

25. The isolated antagonist of claim 24 wherein the degree of self-complementarity within the stem is at least 80%.

26. The isolated antagonist of claim 25 wherein the degree of self-complementarity within the stem is at least 90%.

27. The isolated antagonist of claim 26 wherein the degree of self-complementarity within the stem is 100%.

28. The isolated antagonist of claim 4 wherein the stem has a length of at least 10 base pairs.

29. The isolated antagonist of claim 28 wherein the stem has a degree of self-complementarity within the stem of at least 70%.

30. An isolated antagonist directed against a bacterial RNA or a precursor thereof, wherein the bacterial RNA has a stem-loop secondary structure, the stem-loop secondary structure is homologous to RNA or DNA host sequences and/or innate bacterial sequences, the bacterial RNA is from mycobacteria, and wherein the degree of identity within the homologous regions of the stem sequences and the innate or bacterial sequences is at least 70% for the strand with the highest homology, coupled to or enclosed by a pharmaceutical carrier which increases the efficacy of the antagonist to enter target cells, wherein said carrier is selected from the group consisting of lipids, liposomes, ferromagnetic nano-particles, viral vectors, bacterial vectors and gene carriers.

31. The isolated antagonist according to claim 30, wherein the degree of identity within the homologous regions of the stem sequences and the innate or bacterial sequences is at least 75% for the strand with the highest homology.

32. An isolated antagonist directed against a bacterial RNA or a precursor thereof, wherein the bacterial RNA has a stem-loop secondary structure, the stem-loop secondary structure is homologous to RNA or DNA host sequences and/or innate bacterial sequences, and the antagonist is selected from the group consisting of nucleic acid effector molecules, aptamers, and combinations thereof, coupled with or enclosed by a pharmaceutical carrier which increases the efficacy of the antagonist to enter target cells, wherein said carrier is selected from the group consisting of lipids, liposomes, ferromagnetic nano-particles, viral vectors, bacterial vectors and gene carriers.

33. The isolated antagonist according to claim 8, wherein said viral vector is selected from the group consisting of AAV vectors, adenoviral vectors, lentiviral vectors, retroviral vectors, and herpes viral vectors.

34. An isolated antagonist directed against a bacterial RNA or a precursor thereof, wherein the bacterial RNA has a stem-loop secondary structure, the stem-loop secondary structure is homologous to RNA or DNA host sequences and/or innate bacterial sequences, and the antagonist is selected from the group consisting of nucleic acid effector molecules, aptamers and combinations thereof, wherein said nucleic acid effector molecules and aptamers comprise (a) a non-naturally occurring sugar, backbone or nucleobase modified ribonucleotide or deoxyribonucleotide building blocks, (b) lipid residues, (c) cholesterol residues, and/or (d) fluorophors.

35. An isolated antagonist directed against a bacterial RNA or a precursor thereof, wherein the bacterial RNA is homologous or complementary to RNA or DNA host sequences and/or innate bacterial sequences, said antagonist is a modified nucleic acid effector molecule or aptamer, and wherein the modification is selected from the group consisting of (a) a non-naturally occurring sugar, backbone or nucleobase modified ribonucleotide or deoxyribonucleotide building blocks, (b) lipid residues, (c) cholesterol residues, and (d) fluorophors.

36. The isolated antagonist of claim 10 which is covalently linked to a targeting moiety.

37. The isolated antagonist of claim 30, wherein said antagonist is covalently linked to a targeting moiety.

38. The isolated antagonist of claim 32, wherein said antagonist is covalently linked to a targeting moiety.

* * * * *

SEQUENCE LISTING

```
<160> NUMBER OF SEQ ID NOS: 24

<210> SEQ ID NO 1
<211> LENGTH: 86
<212> TYPE: RNA
<213> ORGANISM: Artificial Sequence
<220> FEATURE:
<223> OTHER INFORMATION: miRNA analogous structure derived from
      M.tuberculosis sequences

<400> SEQUENCE: 1
cgccgguucg acaccaagac cgccaucgcc aucagcgccc gcaaauacgc cuuccgcaag     60
cgggugcuga uggcgauggc ggucgu                                          86

<210> SEQ ID NO 2
<211> LENGTH: 76
<212> TYPE: RNA
<213> ORGANISM: Artificial Sequence
<220> FEATURE:
<223> OTHER INFORMATION: miRNA analogous structure derived from
      M.tuberculosis sequences

<400> SEQUENCE: 2
ugagggcgag cagacgcaaa aucgcccauu ucguacccga aaugggcgau uuugcgucug     60
cucgcggaac cuagcg                                                     76

<210> SEQ ID NO 3
<211> LENGTH: 76
<212> TYPE: RNA
<213> ORGANISM: Artificial Sequence
<220> FEATURE:
<223> OTHER INFORMATION: miRNA analogous structure derived from
      M.tuberculosis sequences

<400> SEQUENCE: 3
uaccggccac cagacgcaaa agaacaugau gggcgcacca gcgcccauca uguucuuuug     60
```

-continued

```
cgucugcucg cgaaaa                                                76

<210> SEQ ID NO 4
<211> LENGTH: 81
<212> TYPE: RNA
<213> ORGANISM: Artificial Sequence
<220> FEATURE:
<223> OTHER INFORMATION: miRNA analogous structure derived from
      M.tuberculosis sequences

<400> SEQUENCE: 4
ccggccuagg uucgccgagc gugcgguuuc auccgcacgc ggcggcgcgu cgcggaugaa    60
accgcacgcu cggcgaaagg g                                          81

<210> SEQ ID NO 5
<211> LENGTH: 64
<212> TYPE: DNA
<213> ORGANISM: Artificial Sequence
<220> FEATURE:
<223> OTHER INFORMATION: miRNA candidate

<400> SEQUENCE: 5
cggcgagcag acgcaaaatc gcccaacacg cccgcaaaat gggcgatttt gcgtctgctc    60
gcgc                                                             64

<210> SEQ ID NO 6
<211> LENGTH: 64
<212> TYPE: DNA
<213> ORGANISM: Artificial Sequence
<220> FEATURE:
<223> OTHER INFORMATION: miRNA candidate

<400> SEQUENCE: 6
gcgcgagcag acgcaaaatc gcccatttcg gcacgaaatt gggcgatttt gcgtctgctc    60
gccc                                                             64

<210> SEQ ID NO 7
<211> LENGTH: 64
<212> TYPE: DNA
<213> ORGANISM: Artificial Sequence
<220> FEATURE:
<223> OTHER INFORMATION: miRNA candidate

<400> SEQUENCE: 7
gcgcgagcag acgcagaatc gcacaaaatc agcgattttg atgcgattct gcgtctgctc    60
gcgc                                                             64

<210> SEQ ID NO 8
<211> LENGTH: 64
<212> TYPE: DNA
<213> ORGANISM: Artificial Sequence
<220> FEATURE:
<223> OTHER INFORMATION: miRNA candidate

<400> SEQUENCE: 8
cggcgagcag acgcaaaagc cccctaaacc ggcaggtatt aggggctttt gcgtctgctc    60
gcca                                                             64

<210> SEQ ID NO 9
<211> LENGTH: 64
<212> TYPE: DNA
<213> ORGANISM: Artificial Sequence
<220> FEATURE:
```

<223> OTHER INFORMATION: miRNA candidate

<400> SEQUENCE: 9
cggcgagcag acgcataagc ccccgcacgc acggcgtgtc gggggcttat gcgtctgctc    60
gccg    64

<210> SEQ ID NO 10
<211> LENGTH: 70
<212> TYPE: DNA
<213> ORGANISM: Artificial Sequence
<220> FEATURE:
<223> OTHER INFORMATION: miRNA candidate

<400> SEQUENCE: 10
cggccaccag acgcaaaaga acatgatggg cgcaccagcg cccatcatgt tcttttgcgt    60
ctgctcgcga    70

<210> SEQ ID NO 11
<211> LENGTH: 25
<212> TYPE: DNA
<213> ORGANISM: Homo sapiens
<220> FEATURE:
<221> NAME/KEY: misc_feature
<223> OTHER INFORMATION: myelin protein zero (P0) minus-strand DNA

<400> SEQUENCE: 11
gcccatcatg ttcttgaggg cgttt    25

<210> SEQ ID NO 12
<211> LENGTH: 37
<212> TYPE: DNA
<213> ORGANISM: homo sapiens
<220> FEATURE:
<221> NAME/KEY: misc_feature
<223> OTHER INFORMATION: MHC II minus-strand DNA

<400> SEQUENCE: 12
atcagggaaa tgcaaaagaa catgatgtaa tagcact    37

<210> SEQ ID NO 13
<211> LENGTH: 34
<212> TYPE: DNA
<213> ORGANISM: homo sapiens
<220> FEATURE:
<221> NAME/KEY: misc_feature
<223> OTHER INFORMATION: MHC II plus-strand DNA

<400> SEQUENCE: 13
gtgctattac atcatgttct tttgcatttc cctg    34

<210> SEQ ID NO 14
<211> LENGTH: 20
<212> TYPE: RNA
<213> ORGANISM: artificial sequence
<220> FEATURE:
<223> OTHER INFORMATION: siRNA

<400> SEQUENCE: 14
agacgcaaaa gaacaugaug    20

<210> SEQ ID NO 15
<211> LENGTH: 20
<212> TYPE: RNA
<213> ORGANISM: artificial sequence
<220> FEATURE:

```
<223> OTHER INFORMATION: siRNA

<400> SEQUENCE: 15
ucauguucuu uugcgucugc                                              20

<210> SEQ ID NO 16
<211> LENGTH: 56
<212> TYPE: DNA
<213> ORGANISM: homo sapiens
<220> FEATURE:
<221> NAME/KEY: misc_feature
<223> OTHER INFORMATION: myelin protein zero (P0) plus-strand DNA

<400> SEQUENCE: 16
agcctcaaaa acgccctcaa gaacatgatg ggcctgaact cggacaagtg atcgcc      56

<210> SEQ ID NO 17
<211> LENGTH: 56
<212> TYPE: RNA
<213> ORGANISM: homo sapiens
<220> FEATURE:
<221> NAME/KEY: misc_feature
<223> OTHER INFORMATION: myelin protein zero (P0) mRNA

<400> SEQUENCE: 17
agccucaaaa acgcccucaa gaacaugaug ggccugaacu cggacaagug aucgcc      56

<210> SEQ ID NO 18
<211> LENGTH: 20
<212> TYPE: DNA
<213> ORGANISM: artificial sequence
<220> FEATURE:
<223> OTHER INFORMATION: oligodesoxyribonucleotide (asODN)

<400> SEQUENCE: 18
tttgcgtctg gtggccggta                                              20

<210> SEQ ID NO 19
<211> LENGTH: 46
<212> TYPE: RNA
<213> ORGANISM: Artificial sequence
<220> FEATURE:
<223> OTHER INFORMATION: ribozyme (Hammerhead Ribozym)

<400> SEQUENCE: 19
uuuucgcgag cacugaugag gccgaaaggc cgaaacgcaa aagaac                 46

<210> SEQ ID NO 20
<211> LENGTH: 76
<212> TYPE: RNA
<213> ORGANISM: Artificial Sequence
<220> FEATURE:
<223> OTHER INFORMATION: antisense RNA (asRNA)

<400> SEQUENCE: 20
uuuucgcgag cagacgcaaa agaacaugau gggcgcuggu gcgcccauca uguucuuuug  60
cgucuggugg ccggua                                                  76

<210> SEQ ID NO 21
<211> LENGTH: 21
<212> TYPE: RNA
<213> ORGANISM: Artificial Sequence
<220> FEATURE:
<223> OTHER INFORMATION: siRNA antisense

<400> SEQUENCE: 21
```

```
cagacgcaaa agaacaugag u                                              21

<210> SEQ ID NO 22
<211> LENGTH: 21
<212> TYPE: RNA
<213> ORGANISM: artificial sequence
<220> FEATURE:
<223> OTHER INFORMATION: siRNA sense

<400> SEQUENCE: 22
ucauguucuu uugcgucugu u                                              21

<210> SEQ ID NO 23
<211> LENGTH: 53
<212> TYPE: RNA
<213> ORGANISM: artificial sequence
<220> FEATURE:
<223> OTHER INFORMATION: shRNA-1
<220> FEATURE:
<221> NAME/KEY: misc_feature
<222> LOCATION: (27)..(30)
<223> OTHER INFORMATION: residues 27 to 30 may be included or excluded

<400> SEQUENCE: 23
ucauguucuu uugcgucugu ucaagagaca gacagacgca aaagaacaug agu           53

<210> SEQ ID NO 24
<211> LENGTH: 49
<212> TYPE: RNA
<213> ORGANISM: artificial sequence
<220> FEATURE:
<223> OTHER INFORMATION: shRNA-2

<400> SEQUENCE: 24
cagacgcaaa agaacaugag ucaagaacuc auguucuuuu gcgucuguu               49
```